United States Patent [19]

Ibsen et al.

[11] Patent Number: 4,738,722
[45] Date of Patent: Apr. 19, 1988

[54] DENTAL COMPOSITIONS INCORPORATING GLASS IONOMERS

[75] Inventors: Robert L. Ibsen, Santa Maria; William R. Glace, Orcutt; Donald R. Pacropis, Santa Maria, all of Calif.

[73] Assignee: Den-Mat Corporation, Santa Maria, Calif.

[21] Appl. No.: 907,577

[22] Filed: Sep. 15, 1986

[51] Int. Cl.$^4$ .......................... A61K 6/06; C08L 33/02
[52] U.S. Cl. .................................. 106/35; 260/998.11; 433/228.1; 523/115; 523/116
[58] Field of Search ............ 106/35; 433/226.1, 228.1; 523/115, 116; 260/998.11

[56] References Cited

U.S. PATENT DOCUMENTS

| | | | |
|---|---|---|---|
| 3,814,717 | 6/1974 | Wilson et al. | 260/29.6 M |
| 3,926,646 | 12/1975 | Inoue | 433/226 |
| 4,017,454 | 4/1977 | Muller | 260/998.11 |
| 4,089,830 | 5/1978 | Tezuka et al. | 260/29.6 H |
| 4,209,434 | 6/1980 | Wilson et al. | 260/29.6 H |
| 4,288,355 | 9/1981 | Anderson et al. | 523/116 |
| 4,360,605 | 11/1982 | Schmitt et al. | 523/116 |
| 4,376,673 | 3/1983 | Cheung | 252/142 |
| 4,376,835 | 3/1983 | Schmitt et al. | 523/116 |
| 4,378,248 | 3/1983 | Griffith | 260/998.11 |
| 4,514,342 | 4/1985 | Billington et al. | 433/228.1 |
| 4,527,979 | 7/1985 | McLean et al. | 523/116 |

FOREIGN PATENT DOCUMENTS

| | | | |
|---|---|---|---|
| 1316129 | 5/1973 | United Kingdom | 433/226 |
| 1192826 | 4/1982 | U.S.S.R. | 106/35 |

*Primary Examiner*—Paul Lieberman
*Assistant Examiner*—Linda D. Skaling
*Attorney, Agent, or Firm*—Owen, Wickersham & Erickson

[57] ABSTRACT

A buffered glass ionomer cement for dental use, including in combination, a mixture of a fine particle, 5-10 microns, powder consisting essentially by weight of

| | |
|---|---|
| silica | 20-30% |
| boron oxide | 1-10% |
| aluminum oxide | 10-20% |
| aluminum fluoride | 1-10% |
| calcium fluoride | 30-40% |
| phosphorus pentoxide | 1-5% |
| ammonium fluoride | 1-10% | plus five to twenty percent of the weight of the above of zinc oxide and zero to ten percent of titanium dioxide, and a liquid component comprising, by weight polyacrylic acid of low molecular weight, 40% solution in water—100-80% by weight, d-tartaric acid—0-20%. The powder and the liquid component are mixed together in a ratio of from 1:1 to 5:3 by weight.

7 Claims, No Drawings

DENTAL COMPOSITIONS INCORPORATING GLASS IONOMERS

This invention relates to dental compositions—liners, cements, cores—incorporating glass ionomers.

BACKGROUND OF THE SPECIFICATION

Glass ionomer cements have been in clinical use since 1975 in Europe and were introduced in the U.S. in 1977. See U.S. Pat. No. 4,209,434, issued June 24, 1980. Glass ionomer cements have been generally formulated to two different consistencies, a Type I, for luting of castings, and a Type II, as a restorative.

When introduced into America's dentistry, glass ionomer cements were publicized as the answer to some of dentistry's prayers, because they are tooth-colored, they bond to dentin and enamel, and they contain fluoride ions, which, in theory at least, minimize the occurrence of secondary caries.

The chemical basis of glass ionomer cements is a cross between the silicate cements and the polyacrylic acid cements. The powder portion of the glass ionomers is a finely powdered chemically active glass, such as an aluminosilicate glass, which has been prepared with a fluoride flux, and the liquid portion is a water solution of polyacrylic acid, polymaleic acid, polyitaconic acid, or a copolymer of at least two of these three acids. The glass dissociates into the acid, forming a gel, so that the resultant "cured" material comprises small glass particles suspended in a gel of metal salts of polycarboxylic acids. The reaction of the glass ionomer when the powder is mixed with the liquid containing polyacrylic acid is:

Aluminosilicate glass powder (with fluoride)+ (liquid) polyacrylic acid=polysalt gel matrix+ silica gel coating.

Some of the more recent developments in glass ionomers has have taken the powder portion and coated the glass with a polyacrylic acid solid. The liquid is then water containing a small percent of tartaric acid or a like compound. This formulation has made possible variations in working and setting times, dependent on the particle size of the glass powder or the addition of other reagents to the material.

The setting reaction of the glass ionomer cement can be prolonged to provide a four minute preliminary set and then a more complete setting reaction over the next hour. However, the short preliminary set limits the amount of manipulation of the material during a patient appointment.

At the preliminary stage of setting, the glass ionomer is extremely susceptible to water contamination and dehydration of its own matrix. The material either as a luting agent or a restorative must then be protected by a water resistant varnish during the set. The clinical implications of this requirement will be discussed below.

As time went on, problems inherent in the glass ionomers began to come to light. They were technique-sensitive, sometimes failing in a very short time. They became opaque with time. And, little by little, reports starting appearing about pulpal sensitivity. These reports increased to the point where, in September 1984, the American Dental Association published a precaution position paper on the glass ionomers.

An optimum glass ionomer cement has been sought by the dental industry over the past ten years because the material offers several beneficial advantages over past materials, even though several of the disadvantages have still not been completely overcome. Modifications of technique allow for the use of glass ionomers in combination with other restorative materials to overcome past deficiencies. Glass ionomers are adhesive to calcified tooth structure, both dentin and enamel. They also contain ion-leachable fluoride which affords the addition of protection against decalcification of the surrounding tooth structure to the glass ionomer due to caries.

Glass ionomer cements are not only truly adhesive to both dentin and enamel; they have also shown some adhesion to some of the non-precious alloys currently used in crown and bridge structures. When mixed and handled correctly as a luting agent, they give physical properties superior to that of zinc phosphate cement, and they are biologically compatible with the pulp. However, the biological compatibility of glass ionomer cements has sometimes been in question (JADA, Vol. 109, September 1984). Reports of sensitivity have usually been associated with the cementation of crown and bridge restorations, and the cause of such sensitivity is not known at this time. Theoretically, the post-operative sensitivity is due to the prolonged duration of set of the glass ionomer or due to the hydraulic pressures of cementation where there is minimal thickness of dentin.

Glass ionomers have a protective effect at the margins of a restoration against recurrent decay due to leachable fluoride ions. Studies have shown that this fluoride ion causes a significant decrease in the enamel solubility at the glass ionomer-tooth interface, three times more protective than silicate cements.

Improved adhesion of glass ionomers to tooth structure can be accomplished by using a 25 percent polyacrylic acid cleanser (e.g., DenMat Cavity Cleanser) for ten seconds on the dentin or enamel which is to be bonded to with the glass ionomer. The percent of polyacrylic acid and time of placement is critical to avoid problems with the unclogging of the dentinal tubules. The weak polyacrylic acid cavity cleanser is apparently acting not as an etchant but as a cleanser of loose debris in the dentin smear layer. The removal of this debris is critical for optimal bonding.

The stability of several of the calcium hydroxide restoration products on the market is currently being questioned. When replacing defective composite resin and amalgam restorations, clinicians have reported that the calcium hydroxide base is broken down to a soft consistency. Therefor, research relating to bases and liners have tended to endeavor to find more stable and adhesive dental material. One of these employs glass ionomers, and fast-setting glass ionomer liners are currently available. They have a setting time of three to four minutes and are adhesive to the cavity preparation. The cavity preparation must be moisture-free, and the glass ionomer base or liner must be applied when the surface of the material has a gloss to it. This allows for maximum adhesive bond to the dentin.

Since glass ionomer cements have biologic properties similar to the polycarboxylate cements, they can be used safely for restoring erosion lesions, and as luting agents. However, in deeper cavities it has been recommended that a base of calcium hydroxide or zinc oxide-eugenol, be used.

An additional benefit of a glass ionomer liner or base is that when it is used in conjunction with composite resin restorations it is esthetically compatible, due to the glass ionomer's translucency. The base provides for an intimate seal to the underlying dentin, and the glass ionomer itself has been etched with a gel etchant or phosphoric acid (to control the etchant on just the liner or base) for about a minute. This creates a microretentive surface that allows for an intimate seal of composite resin to glass ionomer, resulting in a restoration sealed from enamel to dentin. Its superior physical properties combined with its adhesion allow for an optimal base or liner under amalgam restorations. The fluoride affords additional protection against recurrence of decay around the base, should the restorative material become defective.

Several manufacturers have been marketing an improved glass ionomer with silver alloy powder incorporated in the glass ionomer matrix. The metal strengthens the glass ionomer without affecting the properties of adhesion to tooth structure and the protection of the leachable fluoride ions. However, silver corrodes; one only has to look at amalgam restorations which are fifty percent silver-alloy powder of the type contained in these glass ionomer mixtures and note the corrosion and weakening of the metal matrix that occurs with the corrosion process. Even when sealed within a tooth, silver shows the tendency to corrode, due to fluid flow within the dentinal tubules, In non-vital teeth, silver endodontic points exhibit this corrosion phenomenon.

Choice of the alloy powder to be added to the glass ionomer should be based on sound metallurgic and biocompatible data. A clinical evaluation of the metals used in prosthetics for removable partial dentures reveals metal alloys which are extremely corrosion resistant in the oral environment with physical properties superior to those of silver alloys. Certainly, such metals would be a better choice for enhancing the glass ionomer cements and allowing for clinical use in select instances as a core material under castings where adequate tooth structure is remaining. There is no need for extensive undercuts to retain the core material, for the glass ionomer will be adhesive.

Generally speaking, glass ionomers have not been good as a surface restorative. The glass ionomers are inferior esthetically to the composite resins. As a restorative, they are extremely sensitive to technique. Any loss of water from the material during setting causes a crazing of the restoration. Water contamination leaves the restorations opaque and chalky in appearance. Glass ionomer restorations are not polishable. The final surface texture is similar to a large particle, quartz-filled first generation composite resin.

Recently, it has been discovered that cured glass ionomers can be acid etched, allowing composite to bond to cured glass ionomers. This "ionomer sandwich" technique allows glass ionomer to be placed against the dentin, where it bonds and obturates, and allows composite to be placed over the ionomer for strength and esthetics.

When glass ionomers are etched, they can be used with the more highly esthetic composite resins to create a superior tooth-colored restoration. The ability to bond composite resin to dentin in conjunction with the dentin bonding ability of glass ionomers gives a superior restoration. The protection of the pulp with a glass ionomer and then application of the composite resin gives a superior esthetic result.

For success with glass ionomers, the following factors are important:

1. The tooth structure to be bonded should be dry and clean of all debris.
2. The glass ionomer should have a glossy appearance before application to the tooth structure.
3. Fast-setting glass ionomers, after the preliminary set, can be cut with rotary instruments in a slightly moist field. During the set of the liners, they should be coated with a water-resistant varnish.
4. Moisture should be excluded during the initial set of a glass ionomer by using a water resistant varnish.
5. A polyacrylic acid cavity cleanser, if used, should be a weak acid (25 percent polyacrylic acid, as compared to using a polyacrylic acid cement liquid which can be in excess of 50 percent polyacrylic acid) which can be applied for 10 seconds, rinsed and dried. The cut tooth surface will then have the loose debris removed without the total removal of the dentin smear layer.

The instances of postoperative sensitivity have occurred only in cases where the glass ionomer cement has been used as a luting agent, particularly for crown and bridge restorations. Also, there is some indication that, in most cases, the thickness of remaining dentin was minimal. As a result, hydraulic pressure created by cementation has been postulated as a possible cause for the sensitivity. A recent study by Pameijer and Stanley compared the pulpal response (in primates) of a glass ionomer cement with a zinc phosphate cement under continuous cementing pressure. Both cements yielded high pulpal response values with the glass ionomer cement appearing more toxic.

Additionally, the setting reaction for glass ionomer cements has been slow, taking some 30 minutes to develop a surface that is resistant to solution. The presence of moisture at this stage can also be deleterious to adequate setting. Therefore, early stress caused by adjusting occlusion or by mastication may cause fracture and subsequent microleakage. Nevertheless, the exact cause for that postoperative sensitivity has remained speculative.

It has been recommended that clinicians apply a thin coating of a lining material locally to those areas of the preparation that come closest to the pulp but not necessarily to the entire preparation. This would be particularly emphasized for preparations with minimal remaining dentin. By focusing on the areas closest to the pulp, the cement's bonding ability to enamel and dentin would not be appreciably diminished. Also, the clinician should keep in mind that proper manipulation of this cement system is critical. Therefore, proper cleaning of the tooth and casting surface, preventing moisture contamination, delaying adjustment for at least 10 minutes, and using the proper powder-to-liquid ratio are recommended to assure good bonding and to reduce the possibility of leakage and pulpal irritation.

SUMMARY OF THE INVENTION

The present invention is a buffered ionomer cement which eliminates the possibility of pupal reaction. This product can be made in a variety of in tooth shades and in a variety of setting times tailored for particular techniques. For luting, set times of over 5 minutes are available, whereas for simple cavities, set times can be provided as low as 1½ minutes. Etching can begin within three minutes of the start of mix.

The buffering may be done by zinc oxide alone or with a mixture of zinc oxide with titanium oxide.

SOME PREFERRED EMBODIMENTS OF THE INVENTION

In general, the invention involves a buffered glass ionomer, having a powder component and a liquid component. Thus, the powder component can be in the following proportions:

| Silica | ($SiO_2$) | 20–30% |
|---|---|---|
| Boron oxide | ($B_2O_3$) | 1–10% |
| Aluminum oxide | ($Al_2O_3$) | 10–20% |
| Aluminum fluoride | ($AlF_3$) | 1–10% |
| Calcium fluoride | ($CaF_2$) | 30–40% |
| Ammonium fluoride | ($F_2$ as $NH_4F$) | 1–5% |
| Phosphorus pentoxide | ($P_2O_5$) | 1–10% |

To the resultant glasses, finely-divided zinc oxide can be added at amounts between 5 and 20% to buffer the mixture (when added to water) to a pH between 5 and 7 titanium dioxide can be used in place of about half the amount of the zinc oxide, in a mixture.

The liquid component can be prepared according to the following composition:

| Polyacrylic acid of low molecular weight (e.g., 5100 MW), 40% solution in water | 100–80% |
|---|---|
| d-tartaric acid | 0–20%. |

These powders and liquids can be mixed together in ratios from about 1:1 to about 1.67:1 (5:3). The set times vary from about one and one-half minutes to about twenty minutes. The resultant hard cement is adequate for use as a dental cement and has a more neutral pH than even the zinc oxide or titanium dioxide mixture with zinc oxide not used.

EXAMPLE 1

The following materials were fused together to form a glass and were then fritted and ball-milled to a fine particle size (5–10 microns).

|  | By Weight |
|---|---|
| Silica | 26% |
| Boron oxide | 6% |
| Aluminum oxide | 16% |
| Aluminum fluoride | 6% |
| Calcium fluoride | 37% |
| Phosphorus pentoxide | 4% |
| Ammonium fluoride | 5% |

A liquid was prepared by mixing polyacrylic acid (MW=5100) with water and d-tartaric acid in the ratio of 38:57:5.

To a quantity of the above glass, 10% finely divided zinc oxide was added, and the resultant powder was mixed with the above liquid in the ratio of 3:2. Working time of the resultant paste was 90 seconds, and set-time about 3½ minutes. The resultant material was judged excellent for a glass ionomer liner.

EXAMPLE 2

Finely divided zinc oxide was mixed with the glass from Example 1 in the amount of 5% by weight. When mixed with the liquid of Example 1 in the amount of 3:2, working time was about 2 minutes and set time about 6 minutes. The resultant material was judged excellent for use as a glass ionomer cement.

EXAMPLE 3

Finely divided zinc oxide and titanium dioxide were added to the glass from Example 1 in the amounts of 5% and 5%, respectively. Working time was about 1¾ minutes and set time about 5 minutes. The resultant material was judged excellent for core build-up purposes.

EXAMPLE 4

Powder and liquid were prepared as in Example 1. The pH was determined on this material as well as on six currently available commercial glass ionomer systems. The pH was determined on the powder alone (by extracting with distilled water) and on the freshly mixed powder and liquid before the set mechanism began, and by extraction on the current ionomer one hour after mixing and 24 hours after mixing. Results were as shown in Table I.

TABLE I

| | Ionomer pH Datum | | | |
|---|---|---|---|---|
| Material | pH Ionomer Powder | pH Ionomer and Acid | pH Ionomer 1 Hour | pH Ionomer 24 Hours |
| Material of Example 3 | 8.6 | 4.4 | 5.3 | 5.8 |
| Fuji I | 6.9 | 3.4 | 4.7 | 5.3 |
| Fuji II | 6.9 | 3.1 | 4.8 | 5.4 |
| Espe Cem | 2.4 | 2.7 | 4.8 | 5.8 |
| Espe Bond | 3.5 | 3.7 | 5.1 | 5.9 |
| Shofu | 6.2 | 2.8 | 3.9 | 4.5 |
| G.C. | 6.3 | 3.5 | 5.1 | 6.6 | pH Ionomer Powder - 1 part powder per 8 parts $H_2O$
pH Ionomer and Acid - Before setting
pH Ionomer/1 Hour - After set
pH Ionomer/24 Hour - After set As pulpal trauma can be initiated by acid material and since the pH of the Example 1 material is at all times closer to neutral than for the commercially available materials, it can be seen that pulpal trauma is far less likely with the material of this invention.

EXAMPLE 5

Powder and liquid were prepared as in Example 1. The powder and liquid were mixed together in a ratio of 3:2 by weight. Flat disks were prepaed, cured, and acid etched with a 37% phosphoric acid solution for 30 seconds. After 30 seconds, the surface was water rinsed and dried. A commercially available dental composite (Ultra-Bond-Den-Mat Corporation) was cemented to the etched surface in the form of a cylinder 5 mm in diameter and approximately 10 mm long. The samples were stored at 37° C. in water for 24 hours and stressed in shear until failure. The same test was performed on four other commercially available glass ionomer cements. Results were as shown in Table II.

TABLE II

| Ionomer Bonding Ability | | |
|---|---|---|
| Ionomer | Shear Strength (#/in²) | Failure Mode |
| Material of Example 5 | 1605 | Within liner |
| Fuji I | 140 | Interfacial |
| Espe Cement | 0* | Interfacial |
| G.C. Cement | 0* | Interfacial |
| Shofu Cement | 0* | Interfacial |

*Composite capsule separated from substrate before strength test was completed.

It can be seen that the ionomer cement in the present invention offers far greater bonding strengths than those materials presently available. This is extremely important for the currently popular "glass ionomer sandwich" technique.

EXAMPLE 6

Material of the present invention and four other currently available glass ionomer cements were prepared into cylinders 3 mm long by 6 mm in diameter. These samples were stored for various lengths of time and tested for tensile strengths using the diametral method. Results are seen in Table III.

TABLE III

| Ionomer Tensile Strengths | | | | | |
|---|---|---|---|---|---|
| Ionomer | Time | Tensile ($\#/in^2$) | Time | Tensile ($\#/in^2$) | Time | Tensile ($\#/in^2$) |
| Material of Example 6 | 1 hr | 950 | 3 days | 1900 | 3 mo | 2322 |
| Espe Cement | 1 hr | 750 | 3 days | 900 | 3 mo | 1489 |
| Shofu Cement | 1 hr | 900 | 3 days | 1550 | 3 mo | 1659 |
| G.C. Cement | 1 hr | 850 | 3 days | 1350 | 3 mo | — |
| Fuju I | 1 hr | 1050 | 3 days | 1450 | 3 mo | 2333 |

At each time period, the material of the current invention showed strengths higher than the currently available materials with one exception.

EXAMPLE 7

The material of the present invention, Example 1, along with four commercially available glass ionomer cements, were mixed and formed into test samples 4 mm in diameter and 8 mm in length. These samples were stored in water at body temperature for three months and then tested in compression to failure. Results are shown in Table IV and show that the material of the present invention was considerably stronger than any of the commercially available cements tested.

TABLE IV

| Ionomer H$_2$O Tests | | |
|---|---|---|
| Ionomer | Weight | Compression |
| Material of Example 1 | 0.1886 gms/0.1843 gms | 13693 $\#/in^2$ |
| Fuji I | 0.1848 gms/0.1841 gms | 11794 $\#/in^2$ |
| Ketac bond | 0.1978 gms/0.1786 gms (pellet broke) | 2821 $\#/in^2$ |
| G.C. | 0.1740 gms/0.1660 gms | 5488 $\#/in^2$ |

EXAMPLE 8

Powder and liquid were prepared as in Example 1 and seven small portions were mixed together in a ratio of 3:2 by weight. Each of seven small portions of commercially available glass ionomer cements were also mixed together as per manufacturer's instructions.

At one-minute after the start of mix, a drop of 37% orthophosphoric acid etchant was placed on portion number one of each type of cement and the result was observed. This was repeated with successive portions at one-minute intervals. In all cases, the first drop merely diluted the mixture. As each cement came closer to final set, the action of the acid changed from dilution of the sample to disintegration of the sample to an etching action on the cured sample. Results are shown in Table V. Other acids such as citric acid may be used.

TABLE V

| Material | Time at Which Etching Occurred |
|---|---|
| Example 1 | 3 minutes |

TABLE V-continued

| Material | Time at Which Etching Occurred |
|---|---|
| Fuji Type I | 7 minutes |
| Fuji Type II | 6 minutes |
| Ketac Cement | 7 minutes |
| Ketac bond | 5 minutes |
| G C Liner | 6 minutes |
| Shofu | 5 minutes |

In the hands of a dentist, this would mean that etching could occur two minutes sooner with the cement of this invention than with the fastest of the other cements tested.

Various current glass ionomer cements make use of aluminum fluoride type glass with either polymaleic acid or polyacrylic acid with tartaric acid to speed up the reaction. Some users freeze-dry the acid onto the glass and use only water to start the reaction. Others use water and tartaric acid with the major polycarboxylic acid either dried or freeze-dried onto the glass.

By combining zinc oxide with the glass several things were accomplished.

1. The setting reaction became more rapid.
2. When acid-etched for use with a sandwich technique, a rougher surface resulted. These rougher surface provides better bonding between the glass ionomer and the composite placed on top of it;
3. Acid etching can start at least two minutes sooner than with prior-art glass ionomer cements;
4. By varying the amount of zinc oxide, a greater degree of control over the setting reaction is obtained;
5. The pH, from mixing to final set, is closer to neutral, making pulpal irritation much less likely.

It has been found that the maleic acid and itaconic acid touted by some manufacturers led to deteriorated properties when used in the present system.

Another change from the standard glass ionomer, is the addition of titanium dioxide to the core material. This adds strength, provide further control of the setting reaction, and makes the core material readily distinguishable from tooth structure.

Additional comments

The recommended uses of the buffered glass ionomer cements of this invention include: a base or liner under restorative materials, a luting cement, and a core material for a cast restoration where adequate tooth structure remains to help support the casting.

Because of the adhesive nature of these buffered glass ionomers, they are ideal for use as a thin liner under composite resins or dental amalgam or as a thermally insulating base under deep cavity preparations, because they do not need undercuts to retain them.

An added benefit of these buffered glass ionomers fast-set liners is their use under composite resins. They are chemically compatible and they have the ability to be etched with phosphoric acid etchant.

The etching of buffered glass ionomer liners and bases should be done with a high viscosity gel etchant, such as 37% orthophosphoric acid thickened with submicron silica particles thereby avoiding the placement of etchant on sound vital dentin.

When adequate tooth structure remains, these buffered glass ionomer can be used to restore areas of the tooth that will be a core for a cast restoration.

If a portion of an amalgam or composite dislodges during tooth preparation for a crown, the fast setting buffered glass ionomer can be placed in that area and will adhere to the dentin then, there is no need for undercuts. It can also be used to block out undercuts in crown preparations prior to making an impression.

These buffered glass ionomer materials are x-ray opaque when used as liners, restorations, cements, and core build-up materials.

These buffered glass ionomer cements are excellent as a luting medium. They are adhesive to dentin and have physical properties that are equal to or surpass those of zinc phosphate cements.

Thus, these buffered glass ionomer cements of this invention reduce the sensitivity problems and yet have all the beneficial properties of glass ionomers, including adhesion to tooth structure and fluoride protection of the teeth. They have the added benefit of being the only glass ionomer available which is pH buffered with zinc oxide. The latter eliminates any free acid during the setting reaction. They are also fast-setting glass ionomers.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A buffered glass ionomer cement for dental use, including in combination, a mixture of (A) (1) a fine particle, 5–10 microns, powder consisting essentially by weight

| silica | 20–30% |
| --- | --- |
| boron oxide | 1–10% |
| aluminum oxide | 10–20% |
| aluminum fluoride | 1–10% |
| calcium fluoride | 30–40% |
| phosphorus pentoxide | 1–5% |
| ammonium fluoride | 1–10% | said powder being obtained from glass resulting from the fusing together of said silica, boron oxide, aluminum oxide, aluminum fluoride, calcium fluoride, phosphorus pentoxide, and ammonium fluoride, then fritting and ball milling to the fine particle size, 5–10 micron, powder, and (2) five to twenty percent of the weight of (1) of powdered zinc oxide and zero to ten percent of powdered titanium dioxide, added to said powder (1) and mixed therewith only after said fritting and ball milling, and (B) a liquid component comprising, by weight (1) 100–80% by weight of polyacrylic acid of low molecular weight, 40% solution in water and (2) 0–20% of d-tartaric acid, said powder component (A) and said liquid component (B) being mixed together in a ratio of from 1:1 to 5:3 by weight.

2. A buffered glass ionomer cement for dental use, including in combination, a mixture of (A) (1) about three parts by weight of a fine particle, 5–10 microns, powder consisting essentially by weight, approximately, of

| silica | 26% |
| --- | --- |
| boron oxide | 6% |
| aluminum oxide | 16% |
| aluminum fluoride | 6% |
| calcium fluoride | 37% |
| phosphorus pentoxide | 4% |
| ammonium fluoride | 5% | said powder being obtained from glass resulting from the fusing together of said silica, boron oxide, aluminum oxide, aluminum fluoride, calcium fluoride, phosphorus pentoxide, and ammonium fluoride, then fritting and ball milling to the fine particle size, 5–10 micron, powder, and (2) five to ten percent of the weight of (1) of powdered zinc oxide and zero to five percent of powdered titanium dioxide, added to said powder (1) and mixed therewith only after said fritting and ball milling, and (B) about two parts by weight of a liquid component comprising, by weight, 38% of polyacrylic acid of low molecular weight, 57% of water, and 5% d-tartaric acid.

3. The cement of claim 2 containing, as (2), about 5% of zinc oxide and 5% of titanium dioxide.

4. The cement of claim 2 containing, as (2) above 10% of zinc oxide.

5. A method of restoring lesions in a living tooth, comprising the steps of:

placing the buffered glass ionomer of claim 1 in a prepared cavity, then etching with a acid solution, said etching enabling a dental composite restorative to adhere to the glass ionomer cement.

6. The method of claim 5 wherein the acid is orthophosphoric acid.

7. The method of claim 5 wherein the acid is citric acid.

* * * * *